United States Patent [19]

Jung et al.

[11] 3,971,817

[45] July 27, 1976

[54] PROCESS FOR THE MANUFACTURE OF MONOMETHYL-TIN TRICHLORIDE

[75] Inventors: Hans Wolf Jung, Anderten; Rudolf Maul, Lorsch, Hesse; Siegfried Kintopf, Bensheim, Bergstrasse; Wilfried Kloss, Kolmback uber Bensheim; Reinhard Knapp, Heppenheim, Bergstrasse, all of Germany

[73] Assignee: Ciba-Geigy Corporation, Ardsley, N.Y.

[22] Filed: Aug. 7, 1974

[21] Appl. No.: 495,357

[30] Foreign Application Priority Data

Aug. 16, 1973 Switzerland .................... 11804/73

[52] U.S. Cl. .............................................. 260/429.7
[51] Int. Cl.² ............................................. C07F 7/22
[58] Field of Search .................................. 260/429.7

[56] References Cited
UNITED STATES PATENTS

| 3,297,732 | 1/1967 | Banks | 260/429.7 |
| 3,414,595 | 12/1968 | Oakes | 260/429.7 |
| 3,415,857 | 12/1968 | Hoye | 260/429.7 |
| 3,454,610 | 7/1969 | Langer | 260/429.7 |
| 3,459,779 | 8/1969 | Neumann | 260/429.7 |
| 3,519,665 | 7/1970 | Molt et al. | 260/429.7 |
| 3,519,667 | 7/1970 | Molt et al. | 260/429.7 |
| 3,595,892 | 7/1971 | van den Hurk | 260/429.7 |
| 3,824,264 | 7/1974 | Bulten | 260/429.7 |
| 3,862,198 | 1/1975 | Kugele et al. | 260/429.7 |

FOREIGN PATENTS OR APPLICATIONS

| 1,038,838 | 8/1966 | United Kingdom | |
| 958,085 | 5/1964 | United Kingdom | 260/429.7 |

OTHER PUBLICATIONS

Chemical Abstracts vol. 63, 11599h (1965).
J. Organometal. Chem., vol. 6 pp. 522–527 (1966).

*Primary Examiner*—Helen M. S. Sneed
*Attorney, Agent, or Firm*—Charles W. Vanecek

[57] ABSTRACT

In the manufacture of monomethyl-tin trichloride by disproportionation of tin tetrachloride with dimethyl-tin dichloride, high yields are achieved by employing phosphines, arsines and stibines or onium compounds of elements of the fifth main group in the periodic system as the catalyst, optionally together with a co-catalyst.

14 Claims, No Drawings

PROCESS FOR THE MANUFACTURE OF MONOMETHYL-TIN TRICHLORIDE

The invention relates to a process for the manufacture of monomethyl-tin trichloride by disproportionation of dimethyl-tin dichloride and tin tetrachloride in the presence of phosphines, arsines, stibines or onium compounds of elements of the fifth main group in the periodic system as the catalyst, which can optionally be employed together with a co-catalyst.

Organo-tin halides are important intermediate products for the manufacture of PVC stabilisers based on tin alkyls. Particularly advantageous stabilisers are obtained if a high proportion of monoalkyl-tin trihalide is present in the organo-tin starting mixture used for the manufacture.

Organo-tin halides can be manufactured by various known processes. Monoalkyl-tin trichloride is only formed as a byproduct in the direct synthesis from tin and, for example, alkyl chloride. The reaction, described in DT-OS No. 2,228,855, of anhydrous $SnCl_2$ with alkyl chlorides in the presence of organo-antimony compounds also only gives low yields of the desired monoalkyl-tin trichloride.

Although the disproportionation disclosed in DT-AS No. 1,962,301 of tin tetraalkyls with tin tetrachloride gives relatively high yields, the high toxicity and volatility of tin tetramethyl in this reaction is, however, particularly disadvantageous. Also, the tin tetramethyl required as starting material is less easily accessible than dimethyl-tin dichloride.

The catalytic disproportionation of dialkyl-tin dichlorides and tin tetrachloride according to the equation $$R_2SnCl_2 + SnCl_4 \xrightarrow{catalyst} 2\ RSnCl_3$$

is also known. Thus, this process is described in U.S. Pat. No. 3,297,732. The catalytic activity of the catalysts proposed in that patent, for example $BiCl_3$ or $FeCl_2$, and, therefore, the reaction velocities and yields achieved in this reaction, are, however, low. The reaction according to DT-PS No. 1,177,158 in phosphorus oxychloride as the solvent and using $P_2O_5$ as the catalyst, gives high yields. However, in this process, it is a particular disadvantage that the solvent and the catalyst can only be handled with difficulty and also that very long reaction times are required. The disproportionation, described in U.S. Pat. No. 3,454,610, in the presence of dialkylsulphoxides has the disadvantage that stable complexes of dialkylsulphoxides and monoalkyl-tin trichlorides are formed and further stages of chemical processing are necessary in order to isolate the pure monoalkyl-tin trichlorides.

It has now been found that, in the disproportionation of dimethyl-tin dichloride and tin tetrachloride, high yields and high reaction velocities are achieved if the reaction is carried out in the presence of phosphines, arsines, stibines, onium compounds of the elements nitrogen, phosphorus, arsenic or antimony or mixtures thereof as the catalyst, and optionally in the presence of tetramethylene sulphone or phosphorus oxychloride as the co-catalyst. In this it is surprising that the catalysts already known for the manufacture of dialkyl-tin dihalides by direct synthesis from tin and alkyl halides also influence this disproportionation reaction in favour of the formation of monomethyl-tin trichloride. It is further surprising that the elimination of methyl chloride, with the formation of tin dichloride from the resulting monomethyl-tin trichloride can be largely repressed at the relatively high reaction temperatures and that the high yields are obtained in short reaction times.

The subject of the present invention is, therefore, a process for the manufacture of monomethyl-tin trichloride by disproportionation of dimethyl-tin dichloride and tin tetrachloride at temperatures between 80°C and 220°C, in the presence of catalysts, characterised in that 0.1 to 20% by weight, relative to the quantity of the starting components, of a compound, or a mixture of compounds, of the formula I $$R_aEX_b \qquad (1)$$

wherein E represents nitrogen, phosphorus, arsenic or antimony, X represents the halogens chlorine, bromine or iodine, R denotes identical or different, linear or branched, alkyl groups with 1 to 18 carbon atoms, $a$ represents the numbers 3 or 4, and $b$ represents the numbers 0, 1 or 2, and the sum of $a$ and $b$ is equal to 3 or 5, and, if E represents nitrogen, $b$ can only denote 1, is employed as the catalyst, optionally with a cocatalyst.

Preferably, the process is carried out at temperatures of 120° to 150°C, E in formula I denotes phosphorus, arsenic or antimony, R denotes identical or different, linear or branched, alkyl groups with 1 to 4 carbon atoms, and $a$ represents 4 and $b$ represents 1.

A particularly strong catalytic action and therefore high yields and reaction velocities are observed when the onium compounds of phosphorus, arsenic and antimony are used. This catalytic activity can be increased even further by the simultaneous use of a co-catalyst, as a result of which even shorter reaction times for higher yields can be achieved. Example 2 shows, in comparison with Example 1, that, when tetramethylene sulphone is used as the co-catalyst, the yields are between 10 and 20% higher, and at the same time the reaction time is reduced by 2 to 3 hours. It is particularly advantageous to employ a co-catalyst additionally in cases where adequately high yields are achieved only after relatively long reaction times when the catalyst, for example the ammonium compounds, phosphines, arsines or stibines, is used alone. Furthermore, side-reactions, for example the elimination of methyl chloride from the resulting monomethyl-tin trichloride, which occur to an increased extent with longer reaction times, are thereby largely repressed.

Suitable co-catalysts are dipolar, aprotic solvents which do not form stable complexes with the starting materials and the end products during the reaction.

Of the solvents investigated in Example 6, tetramethylene sulphone and phosphorus oxychloride are found to be particularly effective. All other solvents display an unduly high tendency to form complexes, so that the yields, compared with the sole use of the catalyst, either cannot be increased or are even considerably lower. The yields also depend on the quantity of catalyst added. If only 0.1% by weight is employed, the yields are lower. In the range from 0.5 to 10% by weight, the yield remains relatively constant, while beyond 20% by weight the yields fall off once more. It is, therefore, preferable to employ 0.5 to 15% by weight of catalyst.

The yield is also dependent on the quantity of the co-catalyst. The constant range here occurs at an addition of about 7 to 400% by weight. The co-catalyst can, therefore, act as the solvent at the same time. On economic grounds, however, it is preferable to employ 7 to 40% by weight. A mixture of tributylmethylphosphonium chloride and tetramethylene sulphone is found to be particularly advantageous in respect of accessibility and handling and of the yields which can be achieved in proportion to the reaction time. The process is carried out by initially introducing dimethyltin dichloride ($Me_2SnCl_2$) and the catalyst, and optionally the co-catalyst, into a reaction flask equipped with a stirrer, a reflux condenser, a dropping funnel and a thermometer, and heating to 130°–140°C. An equivalent quantity of tin tetrachloride corresponding to the disproportionation equation is then added, with stirring, in such a way that the reaction temperature remains between 125° and 150°C. After the reaction, the reaction mixture is distilled in order to isolate the monomethyl-tin trichloride ($MeSnCl_3$). The process can be carried out under normal pressure or also under a higher pressure.

It is also possible, by means of the process according to the invention, to prepare definite mixtures of $Me_2SnCl_2$ and $MeSnCl_3$, by operating with a deficiency of $SnCl_4$. If a mixture having only a low proportion of $MeSnCl_3$ is prepared, it is sufficient to employ one catalyst, for example a phosphonium halide. In this case, as a result of the excess of $Me_2SnCl_2$ in the starting mixture, a quantitative conversion is achieved within short reaction times. If mixtures having higher proportions of $MeSnCl_3$ are prepared, the additional use of a co-catalyst is preferable.

A particularly advantageous embodiment of the process according to the invention consists of re-using the distillation residue in subsequent reactions. As shown in Example 9, if the residue from the reaction, which contains the catalyst and, if appropriate, the co-catalyst, is recycled, the yields increase to over 90% by volume of $MeSnCl_3$, up to a value which remains constant, as a result of which very good total yields are achieved.

The following examples illustrate the subject of the invention in greater detail, without, however, limiting it.

The percentages by weight of the catalyst quoted relate to the sum of the $Me_2SnCl_2$ and $SnCl_4$ employed; the reaction time is quoted in hours.

The yields of $MeSnCl_3$ in percentages by volume relate to the $SnCl_4$ employed and are determined in the following way:

1 g of the distillate is reacted in ether with butylmagnesium chloride and the resulting mixture of the corresponding tin tetraalkyls is analysed by gas chromatography.

EXAMPLE 1

22 g (0.1 mol) of $Me_2SnCl_2$ and 4.8 g (10% by weight) of one of the catalysts indicated in Table I are initially introduced into a 250 ml three-necked flask equipped with a stirrer, a reflux condenser, a thermometer and a dropping funnel. 26 g (0.1 mol) of $SnCl_4$ are then added, with stirring, at 130°–140°C in portions in such a way that the reaction temperature is between 125° and 150°C. The reaction product is subsequently distilled. The yields and the reaction times are given in Table I.

Table I

| No. | Catalyst | % by weight | Reaction time [hours] | Yield [% by volume] |
|---|---|---|---|---|
| 1 | $Bu_3EtPCl$ | 10 | 5.0 | 61 |
| 2 | $Bu_3n$-$HexPCl$ | 10 | 5.0 | 56 |
| 3 | $Me_3n$-$SteaPCl$ | 10 | 5.0 | 55 |
| 4 | $Me_3n$-$NonPI$ | 10 | 5.0 | 60 |
| 5 | $i$-$Prop_3n$-$DodPCl$ | 10 | 5.0 | 57 |
| 6 | $Bu_3$ $n$-$DodPCl$ | 10 | 5.0 | 59 |
| 7 | $Bu_3MePI$ | 10 | 5.0 | 61 |
| 8 | $Bu_3MePCl$ | 10 | 5.0 | 60 |
| 9 | $Me_4NCl$ | 10 | 5.0 | 26 |
| 10 | $Bu_3MeNCl$ | 10 | 5.0 | 29 |
| 11 | $Bu_3MeNI$ | 10 | 5.0 | 33 |
| 12 | $Et_4SbI$ | 10 | 5.0 | 61 |
| 13 | $Bu_3P$ | 10 | 5.0 | 18 |
| 14 | $Bu_3Sb$ | 10 | 5.0 | 17 |
| 15 | $Bu_3As$ | 10 | 5.0 | 19 |
| 16 | $Bu_4NCl$ | 10 | 5.0 | 27 |
| 17 | $Bu_4AsI$ | 10 | 5.0 | 61 |
| 18 | $Bu_4SbI$ | 10 | 5.0 | 59 |
| 19 | $Bu_4PI$ | 10 | 5.0 | 63 |
| 20 | $Bu_3PI_2$ | 10 | 5.0 | 62 |

Me = methyl  Hex = hexyl
Et = ethyl   Non = nonyl
Prop = propyl  Dod = dodecyl
Bu = butyl   Stea = stearyl

EXAMPLE 2

The reactions are carried out with the same catalysts and with the quantities and under the conditions indicated in Example 1 with an additional 10% by weight of tetramethylene sulphone as the co-catalyst. The yields and the reaction times are indicated in Table II.

Table II

| No. | Catalyst [10% by weight] | Reaction time [hours] | Yield [% by volume] |
|---|---|---|---|
| 1 | $Bu_3EtPCl$ | 2.5 | 79 |
| 2 | $Bu_3n$-$HexPCl$ | 3.0 | 78 |
| 3 | $Me_3$ $n$-$SteaPCl$ | 3.0 | 85 |
| 4 | $Me_3n$-$NonPI$ | 3.0 | 83 |
| 5 | $i$-$Prop_3n$-$Dod$ $PCl$ | 3.0 | 81 |
| 6 | $Bu_3n$-$Dod$ $PCl$ | 3.0 | 79 |
| 7 | $Bu_3MePI$ | 2.0 | 76 |
| 8 | $Bu_3MePCl$ | 2.0 | 86 |
| 9 | $Me_4NCl$ | 5.0 | 61 |
| 10 | $Bu_3MeNCl$ | 2.5 | 75 |
| 11 | $Bu_3MeNI$ | 2.5 | 80 |
| 12 | $Et_4SbI$ | 2.5 | 74 |
| 13 | $Bu_3P$ | 2.5 | 64 |
| 14 | $Bu_3Sb$ | 2.0 | 74 |
| 15 | $Bu_3As$ | 2.0 | 75 |
| 16 | $Bu_4NCl$ | 2.5 | 72 |
| 17 | $Bu_4AsI$ | 2.5 | 81 |
| 18 | $Bu_4SbI$ | 2.5 | 83 |
| 19 | $Bu_4PI$ | 2.5 | 78 |
| 20 | $Bu_3PI_2$ | 2.0 | 78 |

EXAMPLE 3

Dependence of yield on the quantity of catalyst 22 g (0.1 mol) of $Me_2SnCl_2$ are reacted with 26 g (0.1 mol) of $SnCl_4$ under the conditions indicated in Example 1 and varying quantities of $Bu_3MePCl$ are used as the catalyst. The reaction times and yields are indicated in Table III.

Table III

| % by weight of catalyst | Reaction time [hours] | Yield [% by volume] |
|---|---|---|
| 0.1 | 2.5 | 43 |
| 0.5 | 2.5 | 61 |
| 1.0 | 2.5 | 60 |
| 3.0 | 2.5 | 59 |
| 10.0 | 2.5 | 60 |

Table III-continued

| % by weight of catalyst | Reaction time [hours] | Yield [% by volume] |
|---|---|---|
| 20.0 | 2.5 | 51 |

EXAMPLE 4

Dependence of yield on the quantity of catalyst when simultaneously using a constant quantity of co-catalyst.

22 g (0.1 mol) of $Me_2SnCl_2$ and 26 g (0.1 mol) of $SnCl_4$ are reacted under the conditions indicated in Example 1 in the presence of varying amounts of $Bu_3MePCl$ as the catalyst and 10% by weight of tetramethylene sulphone as the co-catalyst. The yields and the reaction times are given in Table IV.

Table 4

| % by weight of catalyst | Reaction time [hours] | Yield [% by volume] |
|---|---|---|
| 0.1 | 2.0 | 68 |
| 0.5 | 2.0 | 76 |
| 1.0 | 2.0 | 84 |
| 3.0 | 2.0 | 82 |
| 10.0 | 2.0 | 85 |
| 20.0 | 2.0 | 67 |

EXAMPLE 5

Dependence of yield on the quantity of co-catalyst when the quantity of catalyst is constant.

22 g (0.1 mol) of $Me_2SnCl_2$ and 26 g (0.1 mol) of $SnCl_4$ are reacted under the conditions indicated in Example 1 in the presence of 10% by weight of $Bu_3MePCl$ as the catalyst and varying amounts of tetramethylene sulphone as the co-catalyst. The yields and reaction times are given in Table V.

Table V

| % by weight of co-catalyst | Reaction time [hours] | Yield [% by volume] |
|---|---|---|
| 1 | 2.0 | 41 |
| 2 | 2.0 | 43 |
| 5 | 2.0 | 52 |
| 10 | 2.0 | 78 |
| 20 | 2.0 | 83 |
| 40 | 2.0 | 87 |
| 100 | 2.0 | 87 |
| 150 | 2.0 | 87 |
| 200 | 2.0 | 84 |
| 300 | 2.0 | 79 |
| 400 | 2.0 | 81 |
| 500 | 2.0 | 73 |

EXAMPLE 6

Dependence of yield on the co-catalyst.

22 g (0.1 mol) of $Me_2SnCl_2$ are reacted with 26 g (0.1 mol) under the conditions described in Example 1 in the presence of 10% by weight of $Bu_3MePCl$ and 10% by weight of various co-catalysts. The reaction time is 2.5 hours. The yields are given in Table VI.

Table VI

| Co-catalyst | Yield (% by volume of $MeSnCl_3$) |
|---|---|
| Tetramethylethylenediamine | 36 |
| Dibutyl ether | 42 |
| Ethylene glycol dimethyl ether | 48 |
| Dimethylformamide | 51 |
| Hexamethylphosphoric acid triamide | 53 |
| Dimethylsulphoxide | 56 |

Table VI-continued

| Co-catalyst | Yield (% by volume of $MeSnCl_3$) |
|---|---|
| Ethylene carbonate | 62 |
| Propylene carbonate | 63 |
| Pyridine | 62 |
| Phosphorus oxychloride | 84 |
| Tetramethylene sulphone | 86 |

EXAMPLE 7

22 g (0.1 mol) of $Me_2SnCl_2$ and 26 g (0.1 mol) of $SnCl_4$ are reacted under the conditions indicated in Example 1 in the presence of 10% by weight of $Bu_3MeNI$ and 10% by weight of $POCl_3$. The reaction time is 2.0 hours and the yield is 70% by volume of $MeSnCl_3$.

EXAMPLE 8

39.6 g (0.18 mol) of $Me_2SnCl_2$ are stirred with 5.2 g (0.02 mol) of $SnCl_4$ and 5 g of $Bu_3MePCl$ for 5 hours at 120°C. The determination of the yield in the distillate indicates a quantitative conversion of the $SnCl_4$ into $MeSnCl_3$. The reaction mixture consists of 79% by volume of $Me_2SnCl_2$ and 21% by volume of $MeSnCl_3$.

EXAMPLE 9

Recycling the residue from the reaction.

220 g (1 mol) of $Me_2SnCl_2$, 50 g of $Bu_3MePCl$ and 50 g of tetramethylene sulphone are initially introduced into a 1 liter flask and are warmed to 140°C. 211 g (0.8 mol) of $SnCl_4$ are then added dropwise over the course of 20 minutes at a temperature of 140° to 150°C and the mixture is then stirred at this temperature for one hour and 40 minutes. 382 g of reaction product are then distilled off under a vacuum of 12 mm Hg, at between 100° and 110°C. A further 220 g of $Me_2SnCl_2$ are added to the distillation residue and are reacted with 211 g of $SnCl_4$ under the same reaction conditions. 413 g of product were distilled off after one hour and 40 minutes.

The process is repeated a further three times. The yields in % by volume of $MeSnCl_3$, relative to the $SnCl_4$ employed, are given in Table VII. The total yield is 1760 g of $MeSnCl_3$ (92%).

Table VII

| Distillate No. | 1 | 2 | 3 | 4 | 5 |
|---|---|---|---|---|---|
| Yield [% by volume] | 78.6 | 87.8 | 96.9 | 98.2 | 97.6 |

What we claim is:

1. Process for the manufacture of monomethyl-tin trichloride b disproportionation of dimethyl-tin dichloride and tin tetrachloride at temperatures between 80°C and 200°C, in the presence of catalysts, characterised in that 0.1 to 20% by weight, relative to the quantity of the starting components, of a compound, or a mixture of compounds, of the formula I $$R_aEX_b \qquad (1)$$

wherein E represents nitrogen, phosphorus, arsenic or antimony, X represents chlorine, bromine or iodine, R denotes identical or different, linear or branched, alkyl groups with 1 to 18 carbon atoms, $a$ represents the numbers 3 or 4, and $b$ represents the numbers 0 or 1 or 2, and the sum of $a$ and $b$ is equal to 3 or 5 and, if E represents nitrogen, $b$ can only denote 1, is employed as the catalyst.

2. Process according to claim 1, characterised in that 0.5 to 15% by weight of the catalyst are employed.

3. Process according to claim 1, characterised in that, in the formula I, R represents identical or different, linear or branched, alkyl groups with 1 to 4 carbon atoms.

4. Process according to claim 1, characterised in that, in the formula I, $a$ represents 4 and $b$ represents 1.

5. Process according to claim 4, characterised in that, in the formula I, E represents phosphorus, arsenic or antimony.

6. Process according to claim 1, characterised in that the residue from the reaction is recycled.

7. Process according to claim 1, characterised in that the reaction is carried out with a deficiency of $SnCl_4$ and mixtures having definite proportions of monomethyl-tin trichloride and dimethyl-tin dichloride are prepared.

8. A process for the manufacture of monomethyl-tin trichloride by disproportionation of dimethyl-tin dichloride and tin tetrachloride at temperatures between 80°C and 200°C, in the presence of catalysts, wherein 0.1 to 20% by weight, relative to the quantity of the starting components, of a compound, or a mixture of compounds, of the formula I

$$R_a E X_b \qquad (I)$$

wherein E represents nitrogen, phosphorus, arsenic or antimony, X represents chlorine, bromine or iodine, R denotes identical or different, linear or branched, alkyl groups with 1 to 18 carbon atoms, $a$ represents the numbers 3 or 4, and $b$ represents the numbers 0 or 1 or 2, and the sum of $a$ and $b$ is equal to 3 or 5 and, if E represents nitrogen, $b$ can only denote 1, is employed as the catalyst and a dipolar, aprotic solvent which does not form stable complexes with the starting materials and the end products during the reaction is employed as a co-catalyst.

9. A process according to claim 8 wherein the co-catalyst is tetramethylene sulphone or phosphorus oxychloride.

10. Process according to claim 8, characterised in that 1 to 400% by weight, relative to the quantity of the starting components, of tetramethylene sulphone or phosphorus oxychloride are employed as the co-catalyst.

11. Process according to claim 10, characterised in that 7 to 40% by weight of the co-catalyst are employed.

12. Process according to claim 10, characterised in that, in the formula I, E represents nitrogen, and tetramethylene sulphone or phosphorus oxychloride is employed as the co-catalyst.

13. Process according to claim 10, characterised in that, in the formula I, $a$ represents 3 and $b$ represents 0, the tetramethylene sulphone or phosphorus oxychloride is employed as the co-catalyst.

14. Process according to claim 11, characterised in that in each case 10% by weight of tributylmethylphosphonium chloride and tetramethylene sulphone are employed.

* * * * *